(12) United States Patent
Yoshida et al.

(10) Patent No.: US 10,383,567 B2
(45) Date of Patent: Aug. 20, 2019

(54) SKIN EVALUATION METHOD AND SKIN EVALUATION DEVICE

(71) Applicant: FUJIFILM Corporation, Tokyo (JP)

(72) Inventors: Naoko Yoshida, Kanagawa (JP); Karin Kuroiwa, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 978 days.

(21) Appl. No.: 14/572,523

(22) Filed: Dec. 16, 2014

(65) Prior Publication Data

US 2015/0105635 A1    Apr. 16, 2015

Related U.S. Application Data

(63) Continuation of application No. PCT/JP2013/065447, filed on Jun. 4, 2013.

(30) Foreign Application Priority Data

Jun. 18, 2012 (JP) .................................. 2012-137107
May 28, 2013 (JP) .................................. 2013-112334

(51) Int. Cl.
*A61B 5/07* (2006.01)
*A61B 5/00* (2006.01)
(Continued)

(52) U.S. Cl.
CPC ............ *A61B 5/441* (2013.01); *A61B 5/0066* (2013.01); *A61B 5/0075* (2013.01);
(Continued)

(58) Field of Classification Search
CPC ...... A61B 5/441; A61B 5/1075; A61B 5/0066; A61B 5/1079; A61B 5/0075;
(Continued)

(56) References Cited

U.S. PATENT DOCUMENTS

2006/0103850 A1* 5/2006 Alphonse ............. A61B 5/0066
356/479
2012/0150001 A1  6/2012 Shakespeare et al.

FOREIGN PATENT DOCUMENTS

JP    2006-000385 A    1/2006
JP    2006-385 A       1/2006
(Continued)

OTHER PUBLICATIONS

Zakharov, P., et al. "Full-field optical coherence tomography for the rapid estimation of epidermal thickness: study of patients with diabetes mellitus type 1." Physiological measurement 31.2 (2009): 193.*

(Continued)

*Primary Examiner* — Navin Natnithithadha
*Assistant Examiner* — Andrey Shostak
(74) *Attorney, Agent, or Firm* — McGinn I.P. Law Group, PLLC.

(57) ABSTRACT

A profile of optical reflectance relative to a depth within a depth range from an epidermis to an upper layer of a dermis is created based on a coherence signal obtained by optical coherence tomography, an evaluation index is determined by calculating a difference between reflectance at a local minimum point and reflectance at a second local maximum point from the created profile, and skin conditions are evaluated based on the evaluation index.

2 Claims, 5 Drawing Sheets

(51) Int. Cl.
*A61B 8/08* (2006.01)
*G01N 21/47* (2006.01)
*A61B 5/107* (2006.01)

(52) U.S. Cl.
CPC .......... *A61B 5/0082* (2013.01); *A61B 5/1075* (2013.01); *A61B 5/1077* (2013.01); *A61B 5/1079* (2013.01); *A61B 5/742* (2013.01); *A61B 8/0858* (2013.01); *G01N 21/4795* (2013.01)

(58) Field of Classification Search
CPC ..... A61B 5/0082; A61B 5/1077; A61B 5/742; A61B 8/0858; G01N 21/4795
See application file for complete search history.

(56) References Cited

FOREIGN PATENT DOCUMENTS

| JP | 2008-65491 A | | 3/2008 | |
|---|---|---|---|---|
| JP | 2011-158395 A | | 8/2011 | |
| JP | 2011158395 A | * | 8/2011 | ............ G01N 21/17 |
| JP | 4790231 B2 | | 10/2011 | |
| WO | WO 2011/135341 A2 | | 11/2011 | |
| WO | WO 2011/135341 A3 | | 11/2011 | |

OTHER PUBLICATIONS

The English-language machine translation of the specification of JP 2011-158395 is attached herewith.*
Korean Office Action dated Dec. 1, 2015 with a partial English translation thereof.
Extended European Search Report dated Jan. 26, 2016.
P. Zakharov et al., "Full-Field Optical Coherence Tomography for the Rapid Estimation of Epidermal Thickness: Study of Patients with Diabetes Mellitus Type 1." Full-field OCT for the rapid estimation of epidermal thickness, Physiological Measurement, Institute of Physics Publishing, Bristol, GB, vo 1 . 31, No. 2, Feb. 1, 2010 pp. 193-205, XP020175815.
International Search Report (ISR) (PCT Form PCT/ISA/210), in PCT/JP2013/065447, dated Aug. 13, 2013.
Japanese Office Action dated Oct. 27, 2015 with a partial English translation thereof.
Chinese Office Action dated Feb. 1, 2016 with an English translation thereof.
English Translation of International Preliminary Report on Patentability in PCT No. PCT/JP2013/065447 dated Dec. 23, 2014.

* cited by examiner

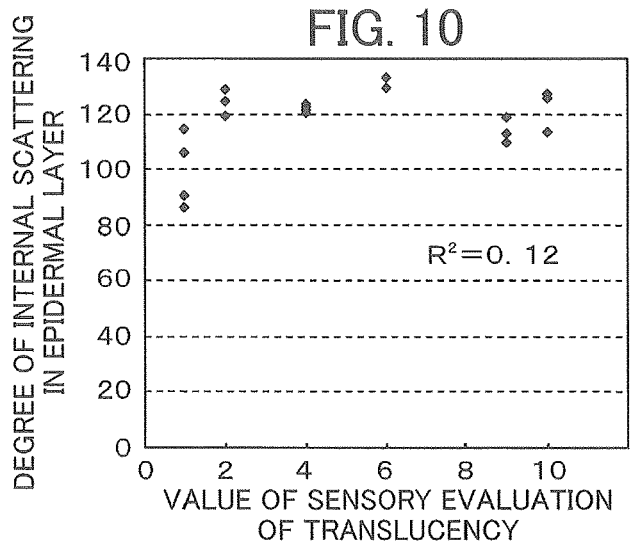
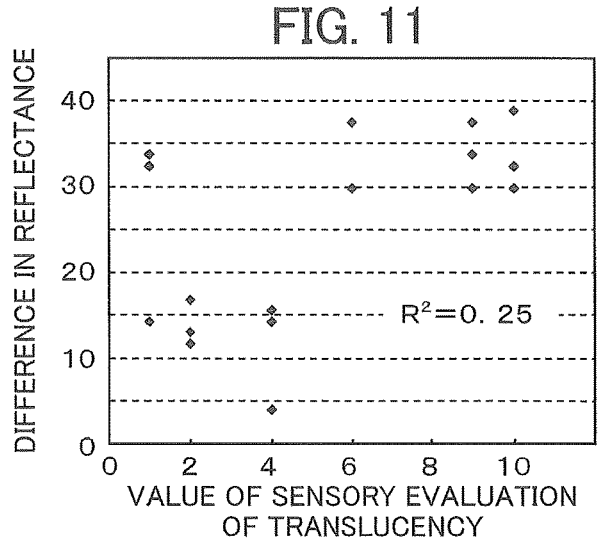
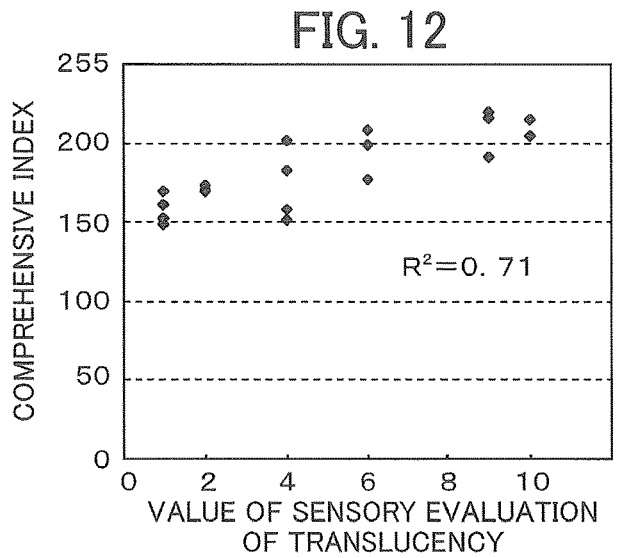

SKIN EVALUATION METHOD AND SKIN EVALUATION DEVICE

CROSS REFERENCE TO RELATED APPLICATIONS

This application is a continuation application of International Application No. PCT/JP2013/065447 filed on Jun. 4, 2013, which claims priority under 35 U.S.C. 119(a) to Application No. 2012-137107 filed in Japan on Jun. 18, 2012 and Application No. 2013-112334 filed in Japan on May 28, 2013, all of which are hereby expressly incorporated by reference into the present application.

BACKGROUND OF THE INVENTION

The present invention relates to a skin evaluation method and a skin evaluation device. In particular, the present invention relates to a skin evaluation method and a skin evaluation device for evaluating skin conditions such as dullness and translucency.

In recent years, as awareness about beauty has been increasing, attention has been focused on various skin conditions such as dullness and translucency. In many cases, dullness is caused over the entire face, around eyes and a mouth, or the like. Dullness refers to, for instance, the decrease in brightness of skin, which makes the skin look dark, or the decrease in ruddy glow of skin, which makes the skin look yellowish.

As a method for measuring the dullness and translucency, there is a method of observing the surface of skin by using a colorimeter for measuring the brightness and color tone of the skin. However, dullness, decrease in translucency, and the like are caused by various factors such as aging, sunburn and saccharification of collagen inside skin, and are greatly affected not only by the conditions at the surface of the skin but also by the conditions at various sites in the skin from the epidermis to the dermis. Accordingly, when only a colorimeter is used for the measurement, the skin conditions cannot be accurately ascertained.

Furthermore, as a technique for analyzing the internal structure of skin, optical coherence tomography (OCT) is known. The optical coherence tomography is for analyzing skin from its surface to a depth of 1 to 2 mm in detail. For instance, in the method of analyzing epidermis proposed by JP 4790231 B, a profile of optical reflectance relative to the depth in skin is created, and the internal structure of the skin is analyzed based on the form of the profile to measure the thickness of the epidermis.

SUMMARY OF THE INVENTION

However, by only analyzing the internal structure of the skin and determining the thickness of the epidermis, it is difficult to know skin conditions such as dullness and translucency.

The present invention has been made to solve the problems of the prior art, and an object thereof is to provide a skin evaluation method and a skin evaluation device that make it possible to accurately evaluate skin conditions such as dullness and translucency.

A skin evaluation method according to the present invention comprises the steps of: detecting coherent light by optical coherence tomography by multiplexing measurement light with which skin is irradiated and which is sequentially reflected from inside of the skin and reference light which moves along an optical path length corresponding to a depth position in the skin at which the measurement light is reflected; creating a profile of optical reflectance relative to a depth within a depth range from an epidermis to an upper layer of a dermis based on a coherence signal obtained by detecting the coherent light; and evaluating skin conditions based on an evaluation index determined according to the profile as created.

In the above, the profile has, as the depth of the skin increases, a first local maximum point that appears at a position corresponding to a point in the uppermost layer of the epidermis, a local minimum point that appears after the first local maximum point and a second local maximum point that appears after the local minimum point.

The evaluation index may be a difference or a ratio between any two out of reflectance at the first local maximum point, reflectance at the local minimum point and reflectance at the second local maximum point.

The evaluation index may be a ratio between a profile area on a shallower side of a certain depth position and a profile area on a deeper side thereof within a range from a lower layer of the epidermis to the upper layer of the dermis. The certain depth position may be a depth position associated with the second local maximum point. The certain depth position may be a depth position associated with the local minimum point. The certain depth position may be a predetermined depth position set in advance.

The evaluation index may be a thickness of the epidermis as determined according to the profile. The thickness of the epidermis is preferably determined by a thickness from a surface of the epidermis to the depth position associated with the second local maximum point.

The evaluation index may be a degree of internal scattering in the epidermis as determined according to the profile. The degree of internal scattering in the epidermis is preferably calculated from an average or non-uniformity of optical reflectance within a depth range from the surface of the epidermis to the depth position associated with the second local maximum point.

The evaluation index may be a comprehensive index created by combining at least two out of a reflectance difference or a reflectance ratio between any two selected from among the first local maximum point, the local minimum point and the second local maximum point, a ratio between a profile area on a shallower side of a certain depth position and a profile area on a deeper side thereof within a range from a lower layer of the epidermis to the upper layer of the dermis, a thickness of the epidermis as determined according to the profile, and a degree of internal scattering in the epidermis as determined according to the profile.

The comprehensive index may be created by combining a reflectance difference between the local minimum point and the second local maximum point, the thickness of the epidermis as determined according to the profile and the degree of internal scattering in the epidermis as determined according to the profile.

The measurement light with which the skin is irradiated may be near infrared light. The measurement light with which the skin is irradiated may be visible light.

A skin evaluation device according to the present invention comprises: a light source configured to emit emission light; a probe configured to irradiate skin with measurement light and receive reflected light sequentially reflected from inside of the skin which has been irradiated with the measurement light; an optical path length adjusting unit configured to adjust an optical path length of reference light such that the optical path length is substantially identical to an optical path length of the reflected light received by the probe; a dividing and multiplexing unit optically connected to the light source, the probe and the optical path length adjusting unit, the dividing and multiplexing unit configured to divide the emission light emitted from the light source into measurement light and reference light to supply the measurement light and the reference light to the probe and the optical path length adjusting unit, respectively, and generate coherent light by multiplexing the reflected light received by the probe and the reference light whose optical path length has been adjusted by the optical path length adjusting unit; a coherent light detecting unit configured to detect the coherent light generated by the dividing and multiplexing unit;

a signal processing unit configured to create a profile of optical reflectance relative to a depth within a depth range from an epidermis to an upper layer of a dermis based on a coherence signal obtained as a result of detection of the coherent light by the coherent light detecting unit; and a skin condition evaluating unit configured to evaluate conditions of the skin based on an evaluation index determined according to the profile created by the signal processing unit.

In the above, the signal processing unit and the skin condition evaluating unit are preferably constituted by a CPU.

The skin evaluation device may further comprise: a storage unit configured to store evaluation results of the skin conditions obtained by the skin condition evaluating unit; and a display unit configured to display the evaluation results of the skin conditions stored in the storage unit.

According to the present invention, a profile of optical reflectance within a depth range from the epidermis to the upper layer of the dermis is created, and the skin conditions are evaluated based on evaluation indices determined in accordance with the profile. Therefore, skin conditions such as dullness and translucency can be accurately evaluated.

BRIEF DESCRIPTION OF THE DRAWINGS

FIG. 2A shows an image obtained by measuring a subject in his/her twenties, and FIG. 2B shows an image obtained by measuring a subject in his/her fifties.

FIG. 3A shows a profile obtained by measuring a subject in his/her twenties; FIG. 3B shows a profile obtained by measuring a subject in his/her thirties; FIG. 3C shows a profile obtained by measuring a subject in his/her forties; and FIG. 3D shows a profile obtained by measuring a subject in his/her fifties.

FIG. 10 is a view showing a correlation between an evaluation index used in a modification example of Embodiment 3 and sensory evaluation.

FIG. 11 is a view showing a correlation between an evaluation index used in another modification example of Embodiment 3 and sensory evaluation.

FIG. 12 is a view showing a correlation between a comprehensive index used in Embodiment 4 and sensory evaluation.

DETAILED DESCRIPTION OF THE INVENTION

Hereinafter, embodiments of the present invention will be described based on the attached drawings.

Embodiment 1

Figure 1:
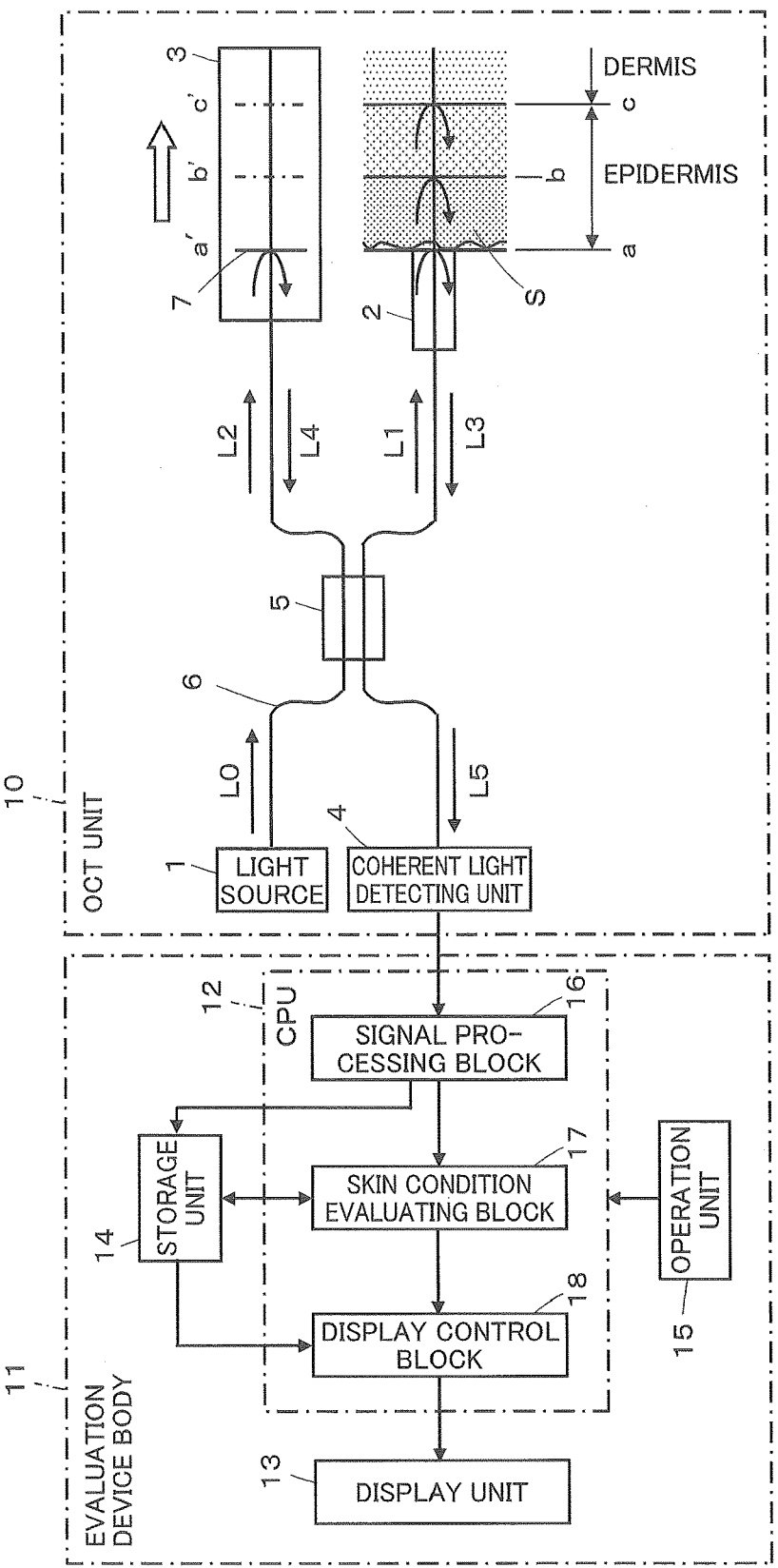
FIG. 1 is a block diagram showing the configuration of a skin evaluation device for implementing a skin evaluation method according to Embodiment 1 of the present invention.

FIG. 1 shows the configuration of a skin evaluation device for implementing a skin evaluation method according to Embodiment 1 of the present invention. The skin evaluation device is for evaluating skin conditions of a subject by optical coherence tomography (OCT). The evaluation device has an OCT unit 10 which irradiates skin with measurement light and selectively detects the light resulting from the measurement light sequentially reflected from the inside of the skin, and an evaluation device body 11 which evaluates the skin conditions of the subject based on the light detected by the OCT unit 10.

The OCT unit 10 has a light source 1 that emits emission light L0; a probe 2 that irradiates skin S with measurement light L1 and receives reflected light L3 generated by the reflection of the measurement light L1 inside the skin S; an optical path length adjusting unit 3 that reflects reference light L2 to generate reference light L4; a coherent light detecting unit 4 that detects coherent light L5; and a dividing and multiplexing unit 5 that is optically connected to each of the light source 1, the probe 2, the optical path length adjusting unit 3 and the coherent light detecting unit 4 to divide the emission light L0 into the measurement light L1 and the reference light L2 and generate the coherent light L5 by multiplexing the reflected light L3 and the reference light L4.

The dividing and multiplexing unit 5 may be connected to each of the light source 1, the probe 2, the optical path length adjusting unit 3 and the coherent light detecting unit 4 by using optical fibers 6.

The light source 1 may be a light source that emits low-coherence light as the emission light L0, such as a super luminescent diode (SLD) or an amplified spontaneous emission (ASE). Such a light source can emit, for example, near infrared light having a wavelength of about 1,300 nm or visible light.

The probe 2 is used in a state where the tip portion thereof is in contact with skin of a subject. The probe 2 irradiates the skin S with the measurement light L1 which has been guided from the dividing and multiplexing unit 5 through the optical fiber 6 and receives the reflected light L3 which is generated by the reflection of the measurement light L1 at each of a plurality of reflection interfaces present at the surface and inside the skin S. The reflected light L3 is guided to the dividing and multiplexing unit 5 from the probe 2 through the optical fiber 6. The probe 2 may be, for example, a probe described in JP 2012-13432 A that is configured to irradiate skin S of a subject with the measurement light L1 while rotating the irradiation direction of the measurement light L1 about a rotation axis lying parallel to the surface of the skin S. Alternatively, a probe may be used in which a portion of emitting the measurement light L1 is composed of a galvano mirror and the like such that skin S is irradiated with the measurement light L1 in a planar manner.

The optical path length adjusting unit 3 is for adjusting the length of optical path of the reference light L2 guided from the dividing and multiplexing unit 5 through the optical fiber 6, and has a reflecting mirror 7 disposed to block the optical path of the reference light L2. The reflecting mirror 7 is moved in a certain direction at a predetermined speed such that the position thereof gradually changes along the optical path of the reference light L2. As a result, the reference light L2 is reflected at various mirror positions and the optical path length thereof varies accordingly. At this time, each of the mirror positions is adjusted to correspond to each of the reflection interfaces on or in the skin S and therefore, the optical path length of the reference light L2 can be adjusted to be substantially identical to the optical path length of the measurement light L1. When the reference light L2 is reflected from the reflecting mirror 7, the reference light L4 is generated, and the reference light L4 is guided to the dividing and multiplexing unit 5 from the optical path length adjusting unit 3 through the optical fiber 6.

The dividing and multiplexing unit 5 may be, for example, a 2×2 optical fiber coupler. The dividing and multiplexing unit 5 divides the emission light L0 emitted from the light source 1 into the measurement light L1 and the reference light L2. Furthermore, the dividing and multiplexing unit 5 generates the coherent light L5 by multiplexing the reflected light L3 and the reference light L4 that have been respectively guided from the probe 2 and the optical path length adjusting unit 3. The coherent light L5 is guided to the coherent light detecting unit 4 from the dividing and multiplexing unit 5 through the optical fiber 6.

The coherent light detecting unit 4 detects the coherent light L5 guided from the dividing and multiplexing unit 5, generates an electric signal corresponding to the intensity of the coherent light L5 and outputs the electric signal to the evaluation device body 11 as a coherence signal.

The evaluation device body 11 has a CPU 12 that is electrically connected to the coherent light detecting unit 4 of the OCT unit 10, and a display unit 13 is connected to the CPU 12. A storage unit 14 and an operation unit 15 are also connected to the CPU 12.

The CPU 12 is composed of a plurality of arithmetic function blocks including a signal processing block 16, a skin condition evaluating block 17 and a display control block 18 which are sequentially connected to one another. The signal processing block 16 is supplied with the coherence signal output from the coherent light detecting unit 4, and creates a profile showing the distribution of optical reflectance at the reflection interfaces on or in the skin S based on intensities of coherence signals and positions of the reflecting mirror 7 of the optical path length adjusting unit 3 corresponding to the coherence signals. In addition, the signal processing block 16 can produce a tomographic image of the skin S based on intensities of coherence signals and positions of the reflecting mirror 7. The created profile and the produced tomographic image of the skin S are supplied to the skin condition evaluating block 17 and also stored in the storage unit 14.

The skin condition evaluating block 17 sets an evaluation index according to the profile created by the signal processing block 16, evaluates the conditions of the skin S such as dullness and translucency of the skin S based on the evaluation index and supplies the evaluation results of the skin conditions to the display control block 18 while storing the evaluation results in the storage unit 14.

The display control block 18 causes the display unit 13 to display the evaluation results of the skin conditions obtained by the skin condition evaluating block 17. The display control block 18 can also cause the display unit 13 to display the tomographic image of the skin S stored in the storage unit 14.

The blocks of the CPU 12, that is, the signal processing block 16, the skin condition evaluating block 17 and the display control block 18 may be each composed of a dedicated processing circuit. Moreover, the signal processing block 16, the skin condition evaluating block 17 and the display control block 18 refer to a signal processing unit, a skin condition evaluating unit and a display control unit in the present invention, respectively.

The display unit 13 includes a display device such as an LCD, for example, and displays the evaluation results of the skin conditions under the control of the display control block 18.

The storage unit 14 stores information such as the evaluation results of the skin conditions input from the CPU 12 and is composed of, for example, a memory.

The operation unit 15 is for allowing an operator to input information and may be composed of a keyboard, a mouse, a trackball, a touch panel or the like.

Next, the skin evaluation method implemented by the skin evaluation device will be described.

First, as shown in FIG. 1, the tip portion of the probe 2 is brought into contact with the skin S of the subject, for example, the surface of the skin S in a region covering the periphery of the mouth and a cheek in which dullness tends to appear, and the emission light L0 is emitted from the light source 1. The emission light L0 above is near infrared light having a wavelength of about 1,300 nm.

The emission light L0 emitted from the light source 1 is guided to the dividing and multiplexing unit 5 through the optical fiber 6 and is divided into the measurement light L1 and the reference light L2 by the dividing and multiplexing unit 5. The measurement light L1 divided by the dividing and multiplexing unit 5 is guided to the probe 2 through the optical fiber 6, while the reference light L2 divided is guided to the optical path length adjusting unit 3 through the optical fiber 6.

The measurement light L1 having reached the probe 2 is emitted to the skin S from the tip portion of the probe 2. The measurement light L1 emitted to the skin S is transmitted through the skin S from the surface to the inside and during the transmission, the measurement light L1 is reflected from a plurality of reflection interfaces present at several depth positions between the uppermost layer of the epidermis and the dermis, for example, reflected from a reflection interface a positioned at the surface of the skin S, a reflection interface b positioned inside the epidermis and a reflection interface c positioned between the epidermis and the dermis. Then, the probe 2 receives the reflected light L3 having been reflected from each of the reflection interfaces a to c, and the reflected light L3 is guided to the dividing and multiplexing unit 5 from the probe 2 through the optical fiber 6.

On the other hand, the reference light L2 guided to the optical path length adjusting unit 3 from the dividing and multiplexing unit 5 is at various mirror positions reflected by the reflecting mirror 7 moving at the predetermined speed in the optical path length adjusting unit 3. At this time, the reflecting mirror 7 is moved to pass mirror positions a' to c' respectively corresponding to the reflection interfaces a to c on or in the skin S. As a result, the optical path length of the reference light L2 reflected at the mirror position a' is substantially identical to the optical path length of the measurement light L1 reflected at the reflection interface a; the optical path length of the reference light L2 reflected at the mirror position b' is substantially identical to the optical path length of the measurement light L1 reflected at the reflection interface b; and the optical path length of the reference light L2 reflected at the mirror position c' is substantially identical to the optical path length of the measurement light L1 reflected at the reflection interface c. In this way, the optical path length of the reference light L2 can be adjusted relative to the optical path length of the measurement light L1. The reference light L4 having been reflected at each of the mirror positions a' to c' is guided to the dividing and multiplexing unit 5 from the optical path length adjusting unit 3 through the optical fiber 6.

After reaching the dividing and multiplexing unit 5, the reflected light L3 and the reference light L4 are multiplexed together in the dividing and multiplexing unit 5, whereby the coherent light L5 is generated. That is, the reflected light L3 having been reflected at the reflection interface a on the skin S and the reference light L4 having been reflected at the mirror position a' are overlapped and interfere with each other; the reflected light L3 having been reflected at the reflection interface b in the skin S and the reference light L4 having been reflected at the mirror position b' are overlapped and interfere with each other; and the reflected light L3 having been reflected at the reflection interface c in the skin S and the reference light L4 having been reflected at the mirror position c' are overlapped and interfere with each other. As a result, the coherent light L5 corresponding to each interference is generated. Thus, the coherent light L5 is generated at an intensity corresponding to the optical reflectance at each of the reflection interfaces a to c.

The coherent light L5 is guided to the coherent light detecting unit 4 from the dividing and multiplexing unit 5 through the optical fiber 6 and is detected in the coherent light detecting unit 4. Subsequently, the coherent light detecting unit 4 outputs a coherence signal corresponding to the coherent light L5 to the evaluation device body 11.

The coherence signal output to the evaluation device body 11 is input to the signal processing block 16 of the CPU 12. The signal processing block 16 produces a tomographic image of the skin S based on the intensity of the coherence signal and the depth position of the reflection interface of the skin S corresponding to the coherence signal. At this time, because the optical path length of the measurement light L1 is identical to the optical path length of the reference light L2, the depth position of the reflection interface of the skin S can be determined based on the mirror position of the reflecting mirror 7 of the optical path length adjusting unit 3.

Figure 2A:
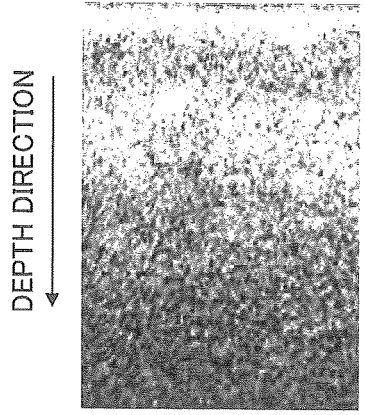
FIGS. 2A and 2B show tomographic images of skins obtained by measuring subjects by the skin evaluation device.
Figure 2B:
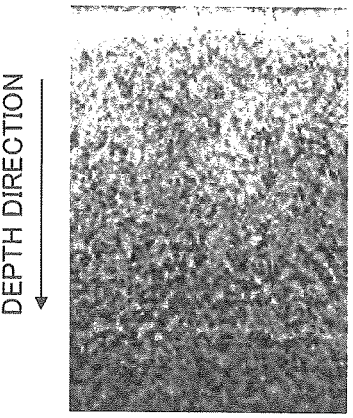

FIGS. 2A and 2B show tomographic images of skins S produced by actually measuring a subject in his/her twenties and a subject in his/her fifties respectively. In these images, sites having a higher reflectance have a higher luminance and thus look whiter, and sites having a lower reflectance have a lower luminance and thus look darker. In each of the tomographic images of the subject in his/her twenties and the subject in his/her fifties, the reflectance changes along the depth direction of the skin S. However, comparing the subject in his/her twenties with the subject in his/her fifties, there is a difference between the subjects in the degree of change in reflectance in the depth direction. The tomographic image of the skin S produced in this way in the signal processing block 16 is stored in the storage unit 14.

In addition, the signal processing block 16 creates a profile of optical reflectance relative to the depth in the skin S based on the intensity of the coherence signal and the depth position of the reflection interface of the skin S corresponding to the coherence signal. FIGS. 3A to 3D each show an example of an actually created profile. FIGS. 3A to 3D respectively show profiles C20, C30, C40 and C50 that are obtained by measuring skins S of subjects (in this example, at a region covering the periphery of the mouth and a cheek for each) in his/her twenties, thirties, forties and fifties. In each of the profiles, depth positions between the surface of the skin S and a depth of 750 μm are plotted on the abscissa, and values of 256-gradation reflectance are plotted on the ordinate. In order to measure age-related skin conditions, specifically, skin conditions such as yellowish dullness and the decrease in translucency, people who hardly show any skin troubles such as sunburn were selected as subjects.

The profile created by the signal processing block 16 is output to the skin condition evaluating block 17 from the signal processing block 16 and also stored in the storage unit 14. Based on the profile, the conditions of the skin S, such as dullness and translucency, are evaluated by the skin condition evaluating block 17.

Figure 3A:
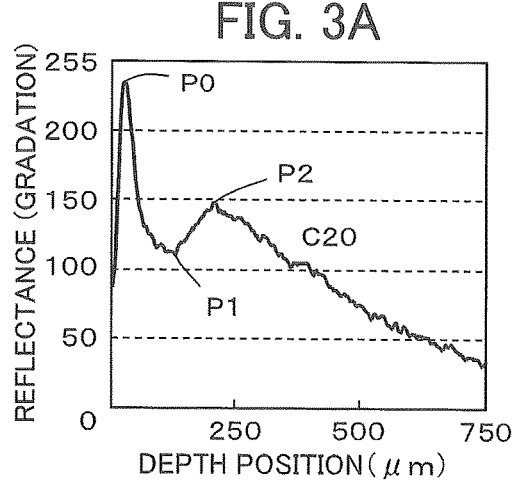
FIGS. 3A to 3D show profiles of optical reflectance obtained by measuring skins of subjects by the skin evaluation device.
Figure 3B:
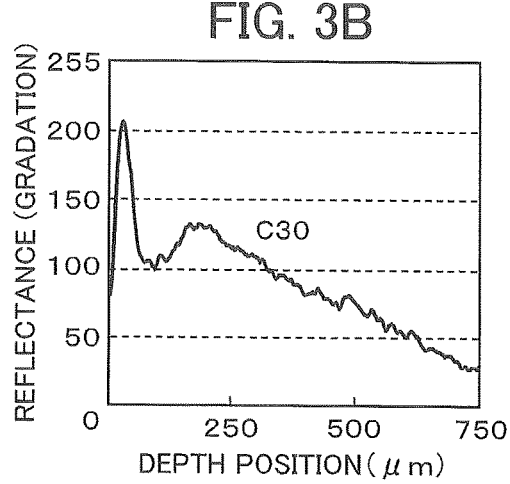

The profiles C20 to C50 of FIGS. 3A to 3D exhibit approximately similar forms with each other. In all of the profiles, for example, as shown in FIG. 3A, as the depth of the skin S from the surface thereof increases, a first local maximum point P0 first appears at a position corresponding to a point in the uppermost layer of the epidermis (a peak portion of the profile that appears at a position corresponding to a point in the surface layer part); a local minimum point P1 appears after the first local maximum point P0 (a valley portion of the profile that appears at a position corresponding to a point within a depth range of about 20 μm to about 200 μm); and a second local maximum point P2 appears after the local minimum point P1 (a peak portion of the profile that appears at a position corresponding to a point within a depth range of about 150 μm to about 300 μm). However, as can be seen in the figures, the profiles C20 to C50 are different in the reflectance at the first local maximum point P0, the local minimum point P1 and the second local maximum point P2 and in the depth positions of the first local maximum point P0, the local minimum point P1 and the second local maximum point P2.

Figure 4:
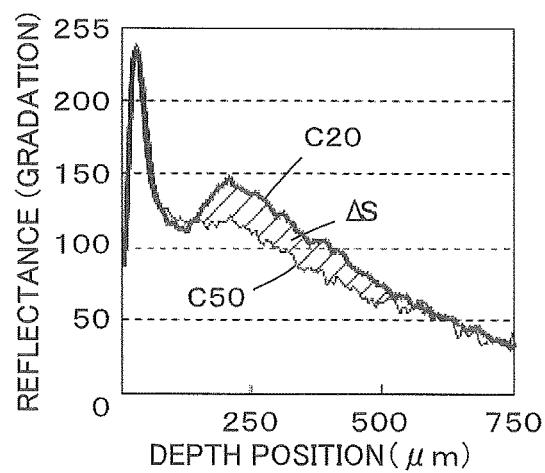
FIG. 4 is a view showing the profile of the subject in his/her twenties that is overlapped and compared with the profile of the subject in his/her fifties.

For example, it can be seen that compared to the profile C20 of the subject in his/her twenties, the reflectance at the second local maximum point P2 sequentially decreases in order of the profile C30 of the subject in his/her thirties, the profile C40 of the subject in his/her forties, and the profile C50 of the subject in his/her fifties. This suggests that the older the subject, the smaller the amount of light returning from the inside of the skin S after being emitted to the skin S. Furthermore, for a more detailed comparison, FIG. 4 is given in which the profile C20 of the subject in his/her twenties is overlapped and compared with the profile C50 of the subject in his/her fifties. As is evident from FIG. 4, the decrease in the reflectance is observed in the profile C50 compared to the profile C20 within a depth range from the surface of skin to a depth of about 500 μm, and an area ΔS of the shaded portion between the profile C20 and the profile C50 indicates the amount of decrease.

Generally, the dullness and decrease in translucency due to aging are known to be caused by the alternation of collagen fibers present in the dermal layer resulting from saccharification or the like, by hypometabolism of cellular components present in the boundary region between the epidermal layer and the dermal layer, and other reasons. In FIG. 4, the depth range from the surface of skin to a depth of about 500 µm, in which a difference in the distribution of the reflectance is observed between the profile C20 and the profile C50, is a range that includes the boundary region between the epidermal layer and the dermal layer, so that the reflectance distribution seems to reflect the skin conditions such as age-related skin dullness and translucency.

Figure 5:
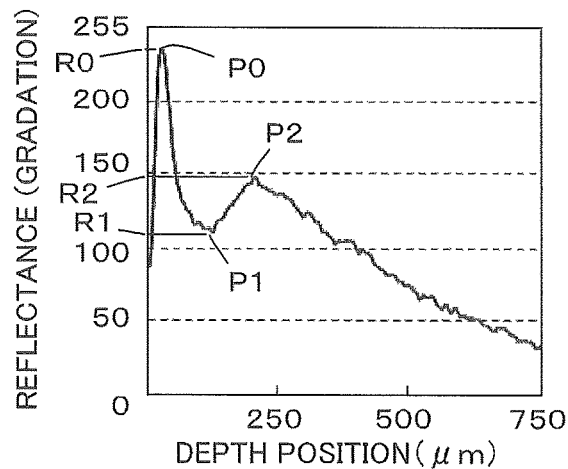
FIG. 5 is a view showing an evaluation index used in Embodiment 1.

Therefore, as show in FIG. 5, for the profile input from the signal processing block 16, the skin condition evaluating block 17 recognizes the first local maximum point P0, the local minimum point P1 and the second local maximum point P2 that sequentially appear as the depth in the skin S from its surface increases, calculates a difference between a reflectance R1 at the local minimum point P1 and a reflectance R2 at the second local maximum point P2 and evaluates the conditions of the skin S such as dullness and translucency by using the difference as an evaluation index.

In this way, the conditions of the skin S are evaluated based on the reflectance R2 at the second local maximum point P2 where the change in the optical reflectance most obviously appears in association with varying conditions of the skin S in terms of dullness and translucency. Consequentially, the conditions of the skin S can be evaluated with high accuracy.

When the first local maximum point P0, the local minimum point P1 and the second local maximum point P2 are recognized, it is preferable to perform processing for inhibiting noise-induced reflectance fluctuation on the profile input from the signal processing block 16.

For instance, the profile input from the signal processing block 16 may be averaged in the direction of measurement position so that the first local maximum point P0, the local minimum point P1 and the second local maximum point P2 are recognized from the averaged profile and that the difference in reflectance is calculated based on the averaged values. Alternatively, the profile input from the signal processing block 16 may be subjected to smoothing processing so that the positions of the first local maximum point P0, the local minimum point P1 and the second local maximum point P2 are recognized from the profile having undergone the processing, while the difference in reflectance is calculated based on values corresponding to the recognized positions in the profile before the smoothing processing and.

In this way, by performing the processing for inhibiting noise-induced reflectance fluctuation, the values of the first local maximum point P0, the local minimum point P1 and the second local maximum point P2 can be accurately determined from the profile, and the conditions of the skin S such as dullness and translucency can be evaluated with high accuracy.

The evaluation results of the conditions of the skin S obtained by the skin condition evaluating block 17 is output to the display control block 18 and also stored in the storage unit 14. The display control block 18 causes the display unit 13 to display thereon either the evaluation results of the conditions of the skin S output from the skin condition evaluating block 17 or the evaluation results of the conditions of the skin S stored in the storage unit 14. Moreover, the display control block 18 can also cause the display unit 13 to display thereon the evaluation results of the conditions of the skin S together with the tomographic image of the skin S stored in the storage unit 14.

According to the present embodiment, with the use of OCT, the conditions of the skin S are evaluated based on the optical reflectance not only at the surface of the skin S but also at the inside of the skin S. Therefore, the conditions of the skin S such as dullness and translucency can be accurately evaluated.

In the foregoing embodiment, the skin condition evaluating block 17 calculates a difference between the reflectance R1 at the local minimum point P1 and the reflectance R2 at the second local maximum point P2 in the profile and uses the difference as an evaluation index. However, the present invention is not limited to the embodiment as long as the evaluation index showing the distribution of optical reflectance within the depth range from the epidermis to the upper layer of the dermis can be calculated.

For instance, in the profile shown in FIG. 5, the skin condition evaluating block 17 may calculate a difference between reflectance R0 at the first local maximum point P0 that appears in the uppermost layer of the epidermis and the reflectance R1 at the local minimum point P1 to use the difference as an evaluation index. Alternatively, the skin condition evaluating block 17 may calculate a difference between the reflectance R0 at the first local maximum point P0 and the reflectance R2 at the second local maximum point P2 to use the difference as an evaluation index. Still alternatively, the skin condition evaluating block 17 may calculate a ratio between any two out of the reflectance R0 at the first local maximum point P0, the reflectance R1 at the local minimum point P1 and the reflectance R2 at the second local maximum point to use the ratio as an evaluation index.

In this way, the evaluation index is calculated based on the reflectance R0 at the first local maximum point P0, the reflectance R1 at the local minimum point P1 and the reflectance R2 at the second local maximum point P2 at each of which the change in the optical reflectance obviously appears in association with varying dullness, translucency and the like. Therefore, the conditions of the skin S can be accurately evaluated.

Embodiment 2

In the aforementioned Embodiment 1, the skin condition evaluating block 17 can also calculate another evaluation index that reflect the reflectance at the boundary region between the lower layer of the epidermis and the upper layer of the dermis, that is, the region where the change in the skin conditions such as age-related dullness, translucency and the like is assumed to appear to a great extent. Specifically, with the profile, the skin condition evaluating block 17 may calculate a ratio between a profile area S1 on a shallower side of a certain depth position and a profile area S2 on a deeper side thereof within a range from the lower layer of the epidermis to the upper layer of the dermis to use the ratio as an evaluation index.

Figure 6:
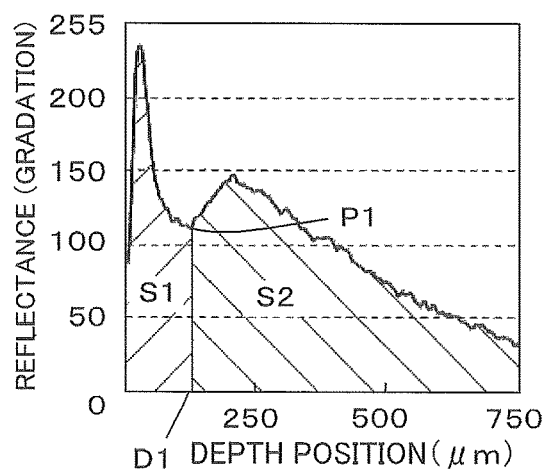
FIG. 6 is a view showing an evaluation index used in Embodiment 2.

For instance, with the profile shown in FIG. 6, a depth position D1 associated with the local minimum point P1 may be determined so that a ratio between a profile area S1 on a shallower side of the depth position D1 and a profile area S2 on a deeper side thereof extending up to a predetermined depth, for example, a depth of 750 µm, is calculated and used as an evaluation index.

Figure 7:
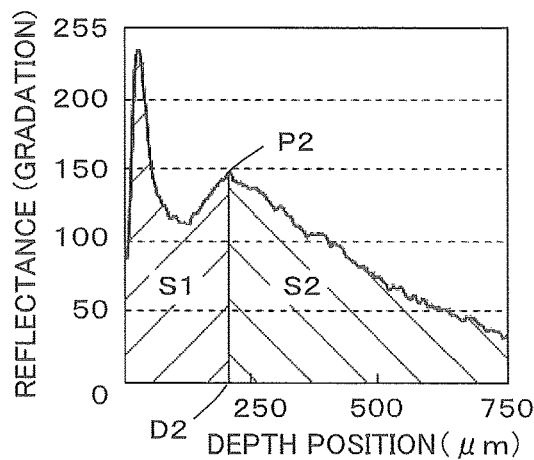
FIG. 7 is a view showing an evaluation index used in a modification example of Embodiment 2.

Alternatively, as shown in FIG. 7, a depth position D2 associated with the second local maximum point P2 of the profile may be determined so that a ratio between a profile area S1 on a shallower side of the depth position D2 and a profile area S2 on a deeper side thereof is calculated and used as an evaluation index.

Figure 8:
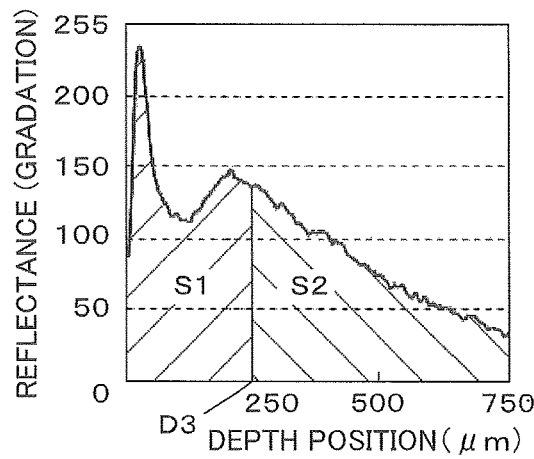
FIG. 8 is a view showing an evaluation index used in another modification example of Embodiment 2.

Still alternatively, as shown in FIG. 8, a predetermined depth position D3 may be set in advance within a depth range from the lower layer of the epidermis to the upper layer of the dermis so that a ratio between a profile area S1 on a shallower side of the predetermined depth position D3 and a profile area S2 on a deeper side thereof is calculated and used as an evaluation index.

In this way, the evaluation index is calculated based on the boundary region between the lower layer of the epidermis and the upper layer of the dermis. Accordingly, age-related change in skin conditions can be accurately evaluated.

The profile area S2 on a deeper side is not limited to the range extending up to a depth of 750 μm, and for example, may be set to extend up to a predetermined depth deeper than a depth of about 500 μm. Alternatively, the profile area S2 may be set to extend up to the deepest part of the measurement range of the skin evaluation device.

Embodiment 3

Figure 3C:
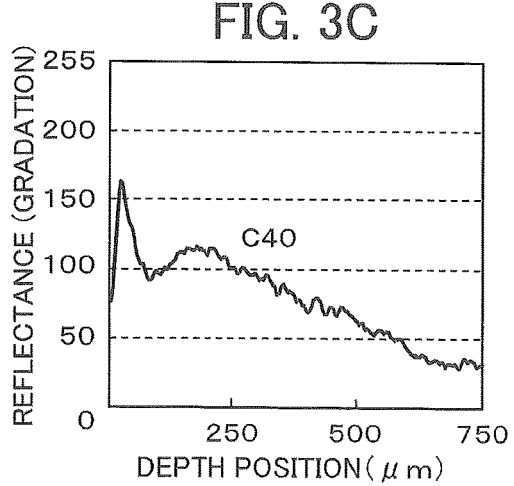
Figure 3D:
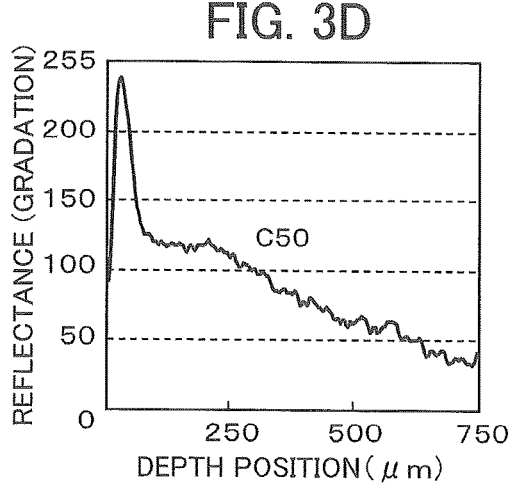

In general, the decrease in the thickness of the epidermis of skin S is known as one factor causing the dullness and the decrease in translucency of the skin S due to aging. Accordingly, the skin condition evaluating block 17 may calculate the thickness of the epidermis from the profile and to use the result as an evaluation index. For instance, the thickness from the surface of the epidermis to the depth position D2 associated with the second local maximum point P2 in a profile may be calculated as the thickness of the epidermis and used as an evaluation index. Actually, the depth position D2 associated with the second local maximum point P2 in the profile C40 of a subject in his/her forties shown in FIG. 3C is positioned shallower than that in the profile C20 of a subject in his/her twenties shown in FIG. 3A, and this shows that the older the subject, the thinner the epidermis.

In addition, the decrease in the degree of internal scattering of light inside the epidermal layer of skin S is known as one factor causing the dullness and the decrease in translucency of the skin S due to aging. Accordingly, the skin condition evaluating block 17 may calculate the degree of internal scattering in the epidermis from the profile and use the result as an evaluation index. For instance, the average of optical reflectance within a depth range from the surface of the epidermis to the depth position D2 associated with the second local maximum point P2 in a profile may be calculated as the degree of internal scattering in the epidermis and used as an evaluation index. Actually, as shown in FIG. 4, the average of the optical reflectance within a depth range up to the depth position D2 associated with the second local maximum point P2 in the profile C50 of a subject in his/her fifties is clearly lower than that in the profile C20 of a subject in his/her twenties, and this shows that the degree of internal scattering in the epidermis decreases with aging. Also, the degree of internal scattering in the epidermis may be obtained by calculating the non-uniformity of optical reflectance within the depth range from the surface of the epidermis to the depth position D2 associated with the second local maximum point P2 in a profile and used as an evaluation index.

In the OCT measurement, a plurality of sites in skin S were irradiated with light and a plurality of profiles were created. As a result, it was found that in accordance with the dullness, the decrease in translucency and the like of the skin S due to aging, the distribution of the reflectance becomes non-uniform depending on the measurement site of the skin S. Therefore, the skin condition evaluating block 17 also may evaluate skin S in consideration of, for example, the degree of non-uniformity of internal scattering of light.

Embodiment 4

In Embodiments 1 to 3, the skin condition evaluating block 17 evaluates the conditions of the skin S such as age-related dullness and translucency. However, the conditions of the skin S to be evaluated are not limited to the age-related conditions, and the conditions of the skin S such as dullness and translucency may be comprehensively evaluated. As an index for comprehensively evaluating dullness and translucency, an index which exhibits a certain correlation with sensory evaluation of dullness and translucency may be used. For example, it is possible to evaluate the degree of dullness and translucency by obtaining a correlation between an index and sensory evaluation by multiple regression analysis or multivariate analysis and using a coefficient of determination.

Figure 9:
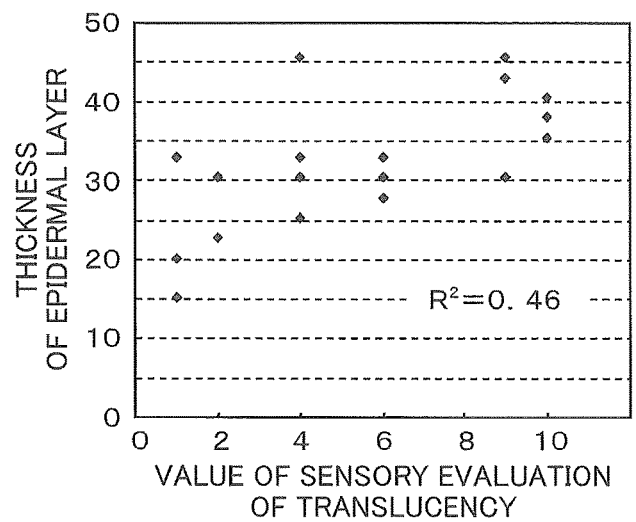
FIG. 9 is a view showing a correlation between the evaluation index used in Embodiment 3 and sensory evaluation.

Correlations between a part of the evaluation indices exemplified in Embodiments 1 to 3 and sensory evaluation values on translucency of the skin S were actually obtained, and the results thereof are shown in FIGS. 9 to 11. In each of FIGS. 9 to 11, the sensory evaluation values on translucency of the skin S obtained by sensory evaluation are plotted on the abscissa, and values of the evaluation index are plotted on the ordinate. The sensory evaluation values are obtained by evaluating translucency of the skin S on a scale of 1 to 10. A value closer to 10 means higher translucency of evaluated skin.

FIG. 9 is a view showing a correlation between the thickness of the epidermis determined from the profile and sensory evaluation. The thickness of the epidermis is calculated using the thickness from the surface of the epidermis to the depth position D2 associated with the second local maximum point P2 in the profile. The correlation between a value indicating the thickness of the epidermis and a value of sensory evaluation was obtained by multiple regression analysis, and as a result, the coefficient of determination is as follows: $R^2=0.46$ FIG. 10 is a view showing a correlation between the degree of internal scattering in the epidermis that is determined from the profile and sensory evaluation. The degree of internal scattering in the epidermis is calculated from the average of the optical reflectance within a depth range from the surface of the epidermis to the depth position D2 associated with the second local maximum point P2 in the profile. The correlation between a value indicating the degree of internal scattering in the epidermis and a value of sensory evaluation was obtained by multiple regression analysis, and as a result, the coefficient of determination is as follows: $R^2=0.12$ FIG. 11 is a view showing a correlation between a difference in optical reflectance, specifically, a difference between the reflectance R1 at the local minimum point P1 of the profile and the reflectance R2 at the second local maximum point P2 of the profile, and sensory evaluation. The correlation between the difference in reflectance and a value of sensory evaluation was obtained by multiple regression analysis, and as a result, the coefficient of determination is as follows: $R^2=0.25$ In Embodiment 4, in order to more accurately evaluate dullness and translucency, the skin condition evaluating block 17 creates a comprehensive index by combining a plurality of indices, and based on the comprehensive index, the conditions of the skin S are evaluated. Specifically, the comprehensive index may be created by combining at least two out of a reflectance difference or a reflectance ratio between any two selected from among the first local maximum point P0, the local minimum point P1 and the second local maximum point P2 in the profile, a ratio between the profile area S1 on a shallower side of a certain depth position and the profile area S2 on a deeper side thereof within a range from the lower layer of the epidermis to the upper layer of the dermis, the thickness of the epidermis that is determined according to the profile, and the degree of internal scattering in the epidermis that is determined according to the profile.

For instance, the skin condition evaluating block 17 may create the comprehensive index by combining the thickness of the epidermis that is determined according to the profile, the degree of internal scattering in the epidermis that is determined according to the profile, and a difference between the reflectance R1 at the local minimum point P1 of the profile and the reflectance R2 at the second local maximum point P2 thereof, and evaluate the conditions of the skin S based on this comprehensive index.

A correlation between the above comprehensive index and a value obtained by performing sensory evaluation for translucency of the skin S was actually obtained, and the result is shown in FIG. 12. Similarly to FIGS. 9 to 11, sensory evaluation values on translucency of the skin S obtained by sensory evaluation are plotted on the abscissa, and values indicating the comprehensive index are plotted in the ordinate. From FIG. 12, a correlation between the comprehensive index and the sensory evaluation was obtained by multiple regression analysis, and as a result, the coefficient of determination is as follows: $R^2=0.71$ The above results show that the use of the comprehensive index obtained by combining a plurality of evaluation indices makes it possible to perform an evaluation similar to sensory evaluation and to comprehensively evaluate dullness, translucency and the like with high accuracy.

In the aforementioned Embodiments 1 to 4, the signal processing block 16 creates the one-dimensional profile of the optical reflectance relative to the depth within the depth range from the epidermis to the upper layer of the dermis, and based on the profile, the skin condition evaluating block 17 calculates the evaluation index and the comprehensive index and evaluates the skin conditions. However, the skin condition evaluating block 17 may also calculate the evaluation index and the comprehensive index based on a two-dimensional image which is generated by the signal processing block 16 and corresponds to the optical reflectance as shown in FIGS. 2A and 2B for example, to thereby evaluate the skin conditions. For instance, based on the image, the skin condition evaluating block 17 calculates the non-uniformity of the distribution of reflectance that varies depending on the measurement site of the skin S and evaluates the conditions of the skin S based on the non-uniformity. Specifically, the skin condition evaluating block 17 extracts a region corresponding to the epidermis in an image according to the optical reflectance and for the region, calculates as an evaluation index the non-uniformity of the luminance average or the standard deviation/dispersion of luminance of the image according to the reflectance, thereby evaluating the conditions of the skin S.

What is claimed is:

1. A skin evaluation device for evaluating skin conditions of dullness and translucency, comprising:

a light source configured to emit emission light;

a probe configured to irradiate skin with measurement light and receive reflected light sequentially reflected from inside of the skin which has been irradiated with the measurement light;

an optical path length adjusting unit configured to adjust an optical path length of reference light such that the optical path length is substantially identical to an optical path length of the reflected light received by the probe;

a dividing and multiplexing unit optically connected to the light source, the probe and the optical path length adjusting unit, the dividing and multiplexing unit configured to divide the emission light emitted from the light source into measurement light and reference light to supply the measurement light and the reference light to the probe and the optical path length adjusting unit, respectively, and generate coherent light by multiplexing the reflected light received by the probe and the reference light whose optical path length has been adjusted by the optical path length adjusting unit;

a coherent light detecting unit configured to detect the coherent light generated by the dividing and multiplexing unit;

a signal processing unit configured to create a profile of optical reflectance relative to a depth within a depth range from an epidermis to an upper layer of a dermis based on a coherence signal obtained as a result of detection of the coherent light by the coherent light detecting unit; and a skin condition evaluating unit configured to evaluate conditions of the skin based on an evaluation index determined according to the profile created by the signal processing unit, wherein the profile has, as the depth of the skin increases, a first local maximum point that appears at a first position corresponding to a point in an uppermost layer of the epidermis, a local minimum point that appears at a second position after the first local maximum point and a second local maximum point that appears at a third position after the local minimum point, wherein the evaluation index is a difference or a ratio between any two out of reflectance at the first local maximum point, reflectance at the local minimum point and reflectance at the second local maximum point, and wherein the skin condition evaluating unit is configured to subject the profile from the signal processing unit to a smoothing process, to recognize the first local maximum point, the local minimum point and the second local maximum point from the profile having undergone the smoothing process, and to calculate the difference or the ratio in reflectance based on values corresponding to the first position, the second position, and the third position in the profile before the smoothing process.

2. The skin evaluation device according to claim 1, further comprising:

a memory configured to store evaluation results of the skin conditions obtained by the skin condition evaluating unit; and a display unit configured to display the evaluation results of the skin conditions stored in the memory.

* * * * *